US007449484B2

(12) United States Patent
Adams et al.

(10) Patent No.: US 7,449,484 B2
(45) Date of Patent: Nov. 11, 2008

(54) COMPOUNDS

(75) Inventors: Jerry L. Adams, King of Prussia, PA (US); Deborah L. Bryan, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 44 days.

(21) Appl. No.: 11/388,058

(22) Filed: Mar. 23, 2006

(65) Prior Publication Data

US 2006/0166988 A1    Jul. 27, 2006

Related U.S. Application Data

(63) Continuation of application No. 10/432,092, filed on May 20, 2003, now abandoned.

(60) Provisional application No. 60/249,963, filed on Nov. 20, 2000.

(51) Int. Cl.
*A61K 31/4439* (2006.01)
*C07D 401/04* (2006.01)

(52) U.S. Cl. .................................. 514/341; 546/274.1

(58) Field of Classification Search .............. 546/274.1; 514/341
See application file for complete search history.

(56) References Cited

U.S. PATENT DOCUMENTS

| 3,707,475 A | 12/1972 | Lambardino |
| 3,940,486 A | 2/1976 | Fitzi |
| 5,656,644 A | 8/1997 | Adams et al. |

FOREIGN PATENT DOCUMENTS

| WO | WO-99061437 | 12/1999 |
| WO | WO-0137835 | 5/2001 |
| WO | WO-0224680 | 3/2002 |

OTHER PUBLICATIONS

Revesz et al.; SAR of 4-hydrozyalkyl substituted heterocycles as novel p38 Map kinase inhibitors; Bioorganic & Medicinal Chemistry Letters; 2000; 1/11; 1261-1264.

*Primary Examiner*—Patricia L Morris
(74) *Attorney, Agent, or Firm*—John L. Lemanowicz

(57) ABSTRACT

The present invention is directed to novel compounds of Formula (I) for use in the treatment of diseases in a mammal, in which inappropriate, excessive or undesirable angiogenesis has occurred and/or where excessive Tie2 receptor activity has occurred.

6 Claims, No Drawings

COMPOUNDS

This application is a continuation of Ser. No. 10/432,092, filed May 20, 2003 now abandoned which claims priority to Ser. No. 60/249,963, filed Nov. 20, 2000. Both applications are incorporated herein by reference in their entirety.

FIELD OF THE INVENTION

The present invention relates to the treatment of diseases, in a mammal, in which inappropriate, excessive or undesirable angiogenesis has occurred and/or where excessive Tie2 receptor activity has occurred.

BACKGROUND OF THE INVENTION

Chronic proliferative diseases are often accompanied by profound angiogenesis, which can contribute to or maintain an inflammatory and/or proliferative state, or which leads to tissue destruction through the invasive proliferation of blood vessels. (Folkman, EXS 79:1-8, 1997; Folkman, *Nature Medicine* 1:27-31, 1995; Folkman and Shing, *J. Biol. Chem.* 267:10931, 1992).

Angiogenesis is generally used to describe the development of new or replacement blood vessels, or neovascularisation. It is a necessary and physiological normal process by which the vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage (Colville-Nash and Scott, *Ann. Rheum. Dis.*, 51, 919, 1992). In diabetes (and in many different eye diseases), new vessels invade the macula or retina or other ocular structures, and may cause blindness (Brooks et al., *Cell*, 79, 1157, 1994). The process of atherosclerosis has been linked to angiogenesis (Kahlon et al., *Can. J. Cardiol.* 8, 60, 1992). Tumor growth and metastasis have been found to be angiogenesis-dependent (Folkman, *Cancer Biol*, 3, 65, 1992; Denekamp, *Br. J. Rad.* 66, 181, 1993; Fidler and Ellis, *Cell*, 79, 185, 1994).

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis (O'Reilly et al., *Cell*, 79, 315, 1994; Ingber et al., *Nature*, 348, 555, 1990), ocular diseases (Friedlander et al., *Science*, 270, 1500, 1995), arthritis (Peacock et al., *J. Exp. Med.* 175, 1135, 1992; Peacock et al., *Cell. Immun.* 160, 178, 1995) and hemangioma (Taraboletti et al., *J. Natl. Cancer Inst.* 87, 293, 1995).

Angiogenesis signals result from the interaction of specific ligands with their receptors. The Tie1 and Tie2 receptors are single-transmembrane, tyrosine kinase receptors (Tie stands for Tyrosine kinase receptors with immunoglobulin and EGF homology domains). Both were recently cloned and reported by several groups (Dumont et al., *Oncogene* 8:1293-1301, 1993; Partanen et al., *Mol. Cell Biol.* 12:1698-1707, 1992; Sato et al., *Proc. Natl. Acad. Sci. USA* 90:9355-9358, 1993).

Based upon the importance of Tie2 receptors in angiogenesis, inhibition of Tie2 kinase activity is predicted to interrupt angiogenesis, providing disease-specific therapeutic effects. Recently, Lin et al. (*J. Clin. Invest.* 100:2072-2078, 1997) has shown that exogenously administered soluble Tie2 receptor inhibited angiogenesis and cancer growth in animal models. Thus inhibition of Tie2 receptors by other means, such as inhibition of Tie2 receptor kinase activity, is expected to have therapeutic benefit in proliferative diseases involving angiogenesis.

The current application teaches the novel finding that compounds of specific structure can inhibit the kinase activity of the Tie2 receptor, block its signal transduction and thus may be beneficial for proliferative diseases via inhibition of signals for angiogenesis.

SUMMARY OF THE INVENTION

The present invention is the finding that novel compounds can inhibit Tie2 kinase, and that these compounds can be used for inhibition of angiogenesis for the treatment of chronic inflammatory or proliferative or angiogenic diseases which are caused by excessive or inappropriate angiogenesis. The preferred compounds for use as Tie2 receptor kinase inhibitors are those compounds of Formula (I) as noted herein.

This invention relates to the novel compounds of Formula (I) and pharmaceutical compositions comprising a compound of Formula (I) and a pharmaceutically acceptable diluent or carrier.

Accordingly, the present invention provides for the novel compounds of Formula (I) represented by the structure:

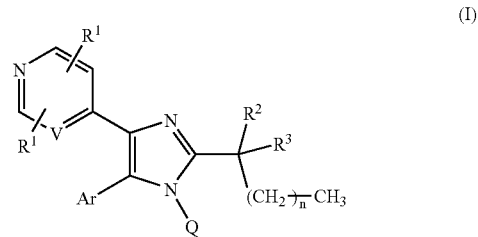

wherein
V is CH or N;
X is O, $CH_2$, S or NH;
n is 0, or an integer having a value of 1 to 4;
t is 0 or an integer having a value of 1 to 10;
Ar is a napth-2-yl, napth-1-yl, a bicyclic or a tricyclic carbocyclic ring, a bicyclic or a tricyclic heteroaromatic ring, or a bicyclic or a tricyclic heterocyclic which ring may be optionally substituted;
Q is hydrogen, $(CR^{13}R^{14})_t OR_9$, $(CR^{13}R^{14})_t OR_{11}$, $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{3-7}$cycloalkyl$C_{1-10}$ alkyl, $C_{5-7}$ cycloalkenyl, $C_{5-7}$ cycloalkenyl $C_{1-10}$ alkyl, aryl, aryl$C_{1-10}$ alkyl, heteroaryl, heteroaryl$C_{1-10}$ alkyl, heterocyclyl, heterocyclyl $C_{1-10}$alkyl, $(CR^{13}R^{14})_tS(O)_mR^8$, $(CR^{13}R^{14})_t NHS(O)_2R^8$, $(CR^{13}R^{14})_t NR^{10}R^{11}$, $(CR^{13}R^{14})_t NO_2$, $(CR^{13}R^{14})_tCN$, $(CR^{13}R^{14})_tS(O)_2NR^{10}R^{11}$, $(CR^{13}R^{14})_tC(Z)R^{11}$, $(CR^{13}R^{14})_t OC(Z)R^{11}$, $(CR^{13}R^{14})_tC(Z)OR^{11}$, $(CR^{13}R^{14})_tC(Z)NR^{10}R^{11}$, $(CR^{13}R^{14})_tOC(Z)NR_{11}OR^9$, $(CR^{13}R^{14})_tNR^{10}C(Z)R^{11}$, $(CR^{13}R^{14})_t NR_{10}C(Z) NR^{10}R^{11}$, $(CR^{13}R^{14})_tN(OR^{10})C(Z) NR^{10}R^{11}$, $(CR^{13}R^{14})_tN(OR^{10})C(Z)R_{11}$, $(CR^{13}R^{14})_tC$ (=NOR$^{10}$)R$^{11}$, (CR$^{13}$R$^{14}$)$_t$NR$^{10}$C(=NR$^{15}$)NR$^{10}$R$^{11}$, (CR$^{13}$R$^{14}$)$_t$OC(Z)NR$^{10}$R$^{11}$, (CR$^{13}$R$^{14}$)$_t$NR$^{10}$C(Z)NR$^{10}$R$^{11}$, or (CR$^{13}$R$^{14}$)$_t$NR$^{10}$C(Z)OR$^{10}$; wherein the cycloalkyl, cycloalkylalkyl, aryl, arylalkyl, heteroaryl, heteroarylalkyl, heterocyclic and heterocyclicalkyl groups may be optionally substituted;

R$^1$ is independently hydrogen, X—R$^4$, halogen, hydroxy, optionally substituted C$_{1-6}$ alkyl, optionally substituted C$_{1-6}$alkylsulfinyl, CH$_2$OR$^5$, amino, mono or di-C$_{1-6}$alkyl amino, N(R$^6$)C(O)R$^7$, N(R$^6$)S(O)$_2$R$^8$, or a 5 to 7-membered N-heterocyclyl ring which optionally contains an additional heteroatom selected from O, S and NR$^9$;

R$^2$ and R$^3$ independently represent an optionally substituted C$_{1-6}$alkyl, or R$^2$ and R$^3$ together with the carbon atom to which they are attached form an optionally substituted C$_{3-7}$cycloalkyl or C$_{5-7}$ cycloalkenyl ring, or R$^2$ and R$^3$ together with the carbon atom to which they are attached form an optionally substituted 5 to 7-membered heterocyclyl ring containing up to 3 heteroatoms selected from N, O and S;

R$^4$ is independently C$_{1-6}$alkyl, aryl, arylC$_{1-6}$alkyl, heterocyclyl, heterocyclylC$_{1-6}$alkyl, heteroaryl, or a heteroarylC$_{1-6}$ alkyl moiety, and wherein any of these moieties may be optionally substituted;

R$^5$ is hydrogen, C(Z)R$^{10}$ or optionally substituted C$_{1-6}$alkyl, optionally substituted aryl, optionally substituted arylC$_{1-6}$alkyl, or S(O)$_2$R$^8$;

R$^6$ is hydrogen or C$_{1-6}$alkyl;

R$^7$ is hydrogen, C$_{1-6}$alkyl, C$_{3-7}$cycloalkyl, aryl, arylC$_{1-6}$alkyl, heteroaryl, heteroarylC$_{1-6}$alkyl, heterocyclyl, or heterocyclylC$_{1-6}$alkyl;

R$^8$ is C$_{1-6}$alkyl, C$_{3-7}$cycloalkyl, aryl, arylC$_{1-6}$alkyl, heteroaryl, heteroarylC$_{1-6}$alkyl, heterocyclyl, or heterocyclyl C$_{1-6}$alkyl;

R$^9$ is hydrogen, C$_{1-4}$alkyl, C$_{3-7}$cycloalkyl or aryl;

R$^{10}$ is selected from hydrogen, C$_{1-6}$alkyl, C$_{3-7}$cycloalkyl, C$_{3-7}$cycloalkyl C$_{1-6}$alkyl, aryl, arylC$_{1-6}$alkyl, heterocyclyl, heterocyclylC$_{1-6}$alkyl, heteroaryl and heteroarylC$_{1-6}$alkyl, any of which may be optionally substituted; and R$^{13}$ and R$^{14}$ are independently hydrogen, C$_{1-6}$alkyl, C$_{3-7}$cycloalkyl, C$_{3-7}$cycloalkyl C$_{1-6}$alkyl, aryl, arylC$_{1-6}$alkyl, heterocyclyl, heterocyclylC$_{1-6}$alkyl, heteroaryl, or heteroarylC$_{1-6}$alkyl, any of which may be optionally substituted; or R$^{11}$ and R$^{12}$ together with the nitrogen to which they are attached form a 5 to 7 membered heterocyclic ring optionally containing an additional heteroatom selected from O, S, or NR$^9$;

R$^{15}$ is hydrogen, cyano, C$_{1-4}$ alkyl, C$_{3-7}$ cycloalkyl or aryl;

Z is oxygen or sulfur;

or a pharmaceutically acceptable salt thereof.

DETAILED DESCRIPTION OF THE INVENTION

The present invention is the directed to novel compounds which can inhibit Tie2 kinase, and use of these compounds for inhibition of angiogenesis in the treatment of chronic inflammatory or proliferative or angiogenic diseases which are caused by excessive or inappropriate angiogenesis in a mammal in need thereof.

In the compounds of formula (I), V is suitably CH or N, preferably carbon.

Suitably, the pyridyl or pyrimidine ring is optionally substituted, independently, one to two times independently by the R$^1$ moiety.

Suitably, R$^1$ is independently selected from hydrogen, X—R$^4$, halogen, hydroxy, optionally substituted C$_{1-6}$ alkyl, optionally substituted C$_{1-6}$alkylsulfinyl, CH$_2$OR$^5$, amino, mono or di-C$_{1-6}$alkylamino, N(R$^6$)C(O)R$^7$, N(R$^6$)S(O)$_2$R$^8$, or a 5 to 7-membered N-heterocyclyl ring which optionally contains an additional heteroatom selected from O, S and NR$^9$. Preferably, the pyridyl or pyrimidine is substituted in the 2-position. Preferably, R$^1$ is hydrogen or X—R$^4$.

X is suitably, O, CH$_2$, S or NH. Preferably X is oxygen or nitrogen.

R$^4$ is independently C$_{1-6}$alkyl, aryl, arylC$_{1-6}$alkyl, heterocyclyl, heterocyclylC$_{1-6}$alkyl, heteroaryl, or a heteroarylC$_{1-6}$ alkyl moiety, and wherein any of these moieties may be optionally substituted. Preferably R$^4$ is an optionally substituted alkyl, aryl, arylalkyl, or heterocyclic alkyl group.

When R$^4$ is aryl, it is preferably an optionally substituted phenyl. When R$^4$ is aryl alkyl, it is preferably an optionally substituted benzyl or phenethyl.

When R$^4$ is a heteroaryl or heteroarylC$_{1-6}$alkyl moiety, it is as defined below. Preferably, it is an optionally substituted pyrrole, quinoline, isoquinoline, pyridine, pyrimidine, oxazole, thiazole, thiadiazole, triazole, imidazole, benzimidazole, isoxazole, thiophene, benzothiophene, furan, benzofuran, pyrazole, pyran, quinazolinyl, pyridazine, pyrazine, uracil, oxadiazole, oxathiadiazole, isothiazole, tetrazole, and indazole.

When R$^4$ is a heterocyclyl, or heterocyclylC$_{1-6}$alkyl it is as defined below. Preferably, it is an optionally substituted tetrahydropyrrole, tetrahydropyran, tetrahydrofuran, tetrahydrothiophene (including oxidized versions of the sulfur moiety), pyrrolidine, piperidine, piperazine, morpholine, thiomorpholine (including oxidized versions of the sulfur moiety), imidazolidine and pyrazolidine ring.

These R$^4$ moieties may be optionally substituted one or more times, preferably 1 to 3 times, independently with halogen; C$_{1-4}$ alkyl, such as methyl, ethyl, propyl, isopropyl, or t-butyl; halosubstituted alkyl, such as CF$_3$; hydroxy; hydroxy substituted C$_{1-4}$ alkyl; C$_{1-4}$ alkoxy, such as methoxy or ethoxy; S(O)$_m$alkyl and S(O)m aryl (wherein m is 0, 1, or 2); C(O)OR$^{11}$, such as C(O)C$_{1-6}$alkyl or C(O)OH moieties; C(O); C(O)R$^{11}$; OC(O)R$^8$; O—(CH$_2$)s-O—, such as in a ketal or dioxyalkylene bridge (s is a number having a value of 1 to 5); amino; mono- and di-C$_{1-6}$ alkylsubstituted amino; N(R$^{10}$)C(O)R$^7$; C(O)NR$^{10}$R$^{11}$; cyano; nitro; or an N-heterocyclyl ring which ring has from 5 to 7 members and optionally contains an additional heteroatom selected from oxygen, sulfur or NR$^9$; optionally substituted aryl, such as phenyl; an optionally substituted aryl C$_{1-6}$alkyl, such as benzyl or phenethyl; aryloxy, such as phenoxy; or arylC$_{1-6}$ alkyloxy such as benzyloxy; and wherein these aryl and arylalkyl moieties may themselves by optionally substituted with halogen, C$_{1-6}$ alkyl, alkoxy, S(O)$_m$ alkyl, amino, or mono- and di-C$_{1-6}$ alkyl-substituted amino.

Preferably the R$^4$ moieties are substituted with an amino, mono- or di-C$_{1-6}$alkylsubstituted amino, a heterocyclic alkyl ring, more preferably an N-heterocyclyl (alkyl) ring which ring has from 5 to 7 members and optionally contains an additional heteroatom selected from oxygen, sulfur or NR$^9$, such as morpholino, pyrollidine, piperazine, piperidine, or pyrrolidinone.

Suitably, R$^2$ and R$^3$ independently represent an optionally substituted C$_{1-6}$alkyl, or R$^2$ and R$^3$ together with the carbon atom to which they are attached form an optionally substituted C$_{3-7}$cycloalkyl or C$_{5-7}$ cycloalkenyl ring, or R$^2$ and R$^3$ together with the carbon atom to which they are attached form an optionally substituted 5 to 7-membered heterocyclyl ring containing up to 3 heteroatoms selected from N, O and S. Preferably R$^2$ and R$^3$ independently represent optionally substituted C$_{1-6}$alkyl.

Suitably, n is 0, 1, 2, 3 or 4. Preferably, n is 1.

Suitably, $R^{11}$ is hydrogen, $C_{1-6}$alkyl, $C_{3-7}$cycloalkyl, $C_{3-7}$cycloalkyl $C_{1-6}$alkyl, aryl, aryl$C_{1-6}$alkyl, heterocyclyl, heterocyclyl$C_{1-6}$alkyl, heteroaryl, or heteroaryl$C_{1-6}$alkyl, any of which may be optionally substituted; or $R^{10}$ and $R^{11}$ together with the nitrogen to which they are attached form a 5 to 7 membered heterocyclic ring optionally containing an additional heteroatom selected from O, S, or $NR^9$.

Suitably, $R^{13}$ and $R^{14}$ are independently hydrogen, $C_{1-6}$alkyl, $C_{3-7}$cycloalkyl, $C_{3-7}$cycloalkyl $C_{1-6}$alkyl, aryl, aryl$C_{1-6}$alkyl, heterocyclyl, heterocyclyl$C_{1-6}$alkyl, heteroaryl, or heteroaryl$C_{1-6}$alkyl, any of which may be optionally substituted; or $R^{11}$ and $R^{12}$ together with the nitrogen to which they are attached form a 5 to 7 membered heterocyclic ring optionally containing an additional heteroatom selected from O, S, or $NR^9$.

Suitably, $R^{12}$ is selected from hydrogen, $C_{1-6}$alkyl, $C_{3-7}$cycloalkyl, $C_{3-7}$cycloalkyl $C_{1-6}$alkyl, heterocyclyl, heterocyclyl$C_{1-6}$alkyl, aryl, aryl$C_{1-6}$alkyl, heteroaryl or heteroaryl $C_{1-6}$alkyl, any of which may be optionally substituted. The $R^{10}$ group and $R^{12}$ moieties may be optionally substituted as defined for the alkyl term.

Suitably, $R^5$ is hydrogen, $C(Z)R^{12}$ or optionally substituted $C_{1-6}$alkyl, optionally substituted aryl, optionally substituted aryl$C_{1-6}$alkyl, or $S(O)_2R^8$.

Suitably, $R^6$ is hydrogen or $C_{1-6}$alkyl.

Suitably, $R^7$ is hydrogen, $C_{1-6}$alkyl, $C_{3-7}$cycloalkyl, aryl, aryl$C_{1-6}$alkyl, heteroaryl, heteroaryl$C_{1-6}$alkyl, heterocyclyl, or heterocyclyl$C_{1-6}$alkyl.

Suitably, $R^8$ is $C_{1-6}$alkyl, $C_{3-7}$cycloalkyl, aryl, aryl$C_{1-6}$alkyl, heteroaryl, heteroaryl$C_{1-6}$alkyl, heterocyclyl, or heterocyclyl$C_{1-6}$alkyl.

Suitably, $R^9$ is hydrogen, cyano, $C_{1-4}$alkyl, $C_{3-7}$cycloalkyl or aryl.

Suitably, $R^{10}$ and $R^{12}$ are independently selected from hydrogen, $C_{1-6}$alkyl, $C_{3-7}$cycloalkyl, heterocyclyl, heterocyclyl$C_{1-6}$alkyl, aryl, aryl$C_{1-6}$alkyl, heteroaryl or heteroaryl $C_{1-6}$alkyl, any of which may be optionally substituted.

Suitably, Z is oxygen or sulfur.

Ar is suitably a napth-2-yl, napth-1-yl, a bicyclic or a tricyclic carbocyclic ring, a bicyclic or a tricyclic heteroaromatic ring, or a bicyclic or a tricyclic heterocyclic ring, and wherein any ring in the system may be optionally substituted one or more times as defined herein below. A bicyclic or tricyclic heteroaromatic or heterocyclic ring system may be a fused ring system which includes a carbocyclic ring. For the heteroaromatic ring system, it will be an aromatic ring, for the heterocyclic ring system the carbocyclic ring may be saturated, contain some unsaturation, or be aromatic.

More specifically, Ar as a bicyclic or a tricyclic heterocyclic, or a bicyclic or tricyclic heteroaromatic ring, which includes, but is not limited to, quinoline, isoquinoline, benzoxazole, benzthiazole, benzofuran, dibenzofuran, benzthiaphene, dibenzothiaphene, benzthiadiazole, benztriazole, benzimidazole, thioanthracene, phenoxathine, benzimidazole, indolyl, or quinazolinyl. Ar is preferably a bicyclic or a tricyclic heteroaromatic ring.

Ar as a heterocyclic ring system includes a bicyclo or a tricyclo fused ring system, containing at least one or more aromatic or heteroaromatic rings, and one or more saturated or unsaturated carbocyclic 4-7 membered rings, or one or more saturated or unsaturated rings containing 4-7 members with one or more heteroatoms selected from oxygen, nitrogen or sulfur (including oxidized versions thereof). The ring system must contain at least one heteroatom selected from oxygen, nitrogen or sulfur. The ring system may include from 7 to 14 ring members.

Ar as a heteroaromatic ring system may include at least one aromatic ring and/or one or more heteroaromatic rings, but the ring system must contain one or more heteroatoms selected from oxygen, nitrogen or sulfur. The ring system may include from 8 to 12 members.

Ar as a bicyclic or a tricyclic carbocyclic ring, includes but is not limited to indene, tetraline, or indane derivatives, in addition to the specific napthyl rings as indicated separately. This carbocyclic ring system includes at least one aromatic ring and one or more saturated or unsaturated carbocyclic 4-7 membered rings attached thereto.

The Ar ring may be optionally substituted one or more times, preferably 1 to 3 times, independently, in any ring. Suitable substituents include halogen, $C_{1-6}$alkyl, aryl, aryl $C_{1-6}$alkyl, cycloalkyl, cycloalkyl $C_{1-6}$alkyl, $C_{1-6}$alkoxy$C_{1-6}$alkyl, halosubstituted $C_{1-6}$alkyl, aryl$C_{1-6}$alkoxy, $(CR^{13}R^{14})_t$ $OR^{12}$, nitro, cyano, $(CR^{13}R^{14})_tNR^{10}R^{11}$, $(CR^{13}R^{14})_tNR^{10}C(Z)R^{12}$, $(CR^{13}R^{14})_tC(Z)NR^{10}R^{11}$, $(CR^{13}R^{14})_tCOR^{12}$, $(CR^{13}R^{14})_tZC(Z)R^{12}$, $(CR^{13}R^{14})_tC(Z)OR^{12}$, $(CR^{13}R^{14})_tC(O)NR^{10}R^{11}$, $(CR^{13}R^{14})_tNR^{10}C(Z)NR^{10}R^{11}$, $(CR^{13}R^{14})_tNR^{10}C(=NH)NR^{10}R^{11}$, $(CR^{13}R^{14})_tC(=NH)—NR^{10}R^{11}$, $(CR^{13}R^{14})_tNR_{10}S(O)_2R^8$, $(CR^{13}R^{14})_tS(O)_2NR^{10}R^{11}$, $(CR^{13}R^{14})_tS(O)_mR^{12}$, heterocyclyl, heteroaryl, heterocyclyl$C_{1-6}$alkyl or heteroaryl$C_{1-6}$alkyl.

Suitably t is 0, or an integer having a value of 1 to 10. Preferably t is 0, or 1, more preferably 0.

Suitably, $R^{13}$ and $R^{14}$ are independently hydrogen, or a $C_{1-6}$alkyl.

Preferably, the Ar group is substituted, in any ring, one or more times by halo, cyano, $(CR^{13}R^{14})_tC(Z)NR^{10}R^{11}$, $(CR^{13}R^{14})_tC(Z)OR^{12}$, $(CR^{13}R^{14})_tCOR^{12}$, $(CR^{13}R^{14})_tS(O)_m R^{12}$, $(CR^{13}R^{14})_tOR^{12}$, halo-substituted-$C_{1-6}$alkyl, $C_{1-6}$alkyl, $(CR^{13}R^{14})_tNR^{10}C(Z)R^{12}$, $(CR^{13}R^{14})_t NR^{10}S(O)_2R^8$, $(CR^{13}R^{14})_tS(O)_2NR^{10}R^{11}$, $(CR^{13}R^{14})_tZC(Z)R^{12}$, or $(CR^{13}R^{14})_tNR^{10}R^{11}$.

More preferably, the Ar ring is substituted one or more times by halogen, $S(O)_mR^{12}$, $OR^{12}$, $C_{1-6}$alkyl, halosubstituted $C_{1-6}$alkyl, hydroxy $C_{1-6}$alkyl, and $C_{1-6}$alkoxy, $NR^{10}S(O)_2R^8$, $NR^{10}C(Z)R^{12}$ or $NR^{10}R^{11}$. More preferred substitution is hydroxy; a $C_{1-6}$alkoxy group, such as methoxy; a $C_{1-6}$ alkyl, such as methyl; or halogen, such as fluorine or chlorine.

Preferably the Ar ring is a napthyl ring, more preferably a napth-2-yl ring. If Ar is a bicyclo heteroaryl ring it is preferably a benzothiophene or a benzofuran ring. A preferred ring placement for the napth-2-yl ring is in the 6-position.

For use herein, the term "alkyl", and "alkenyl" groups, individually or as part of a larger group e.g. "alkoxy", may be straight or branched chain radicals containing up to six carbon atoms, unless otherwise limited, including, but not limited to, methyl, ethyl, n-propyl, iso-propyl, n-butyl, sec-butyl, iso-butyl, tert-butyl, and the like. The alkyl and alkenyl groups may be optionally substituted as herein defined.

For use herein, "cycloalkyl" includes cyclic radicals having from three to eight ring carbon atoms, including but not limited to cyclopropyl, cyclopentyl, cyclohexyl, and the like. The cycloalkyl groups may be optionally substituted as herein defined.

For use herein, "cycloalkenyl" includes cyclic radicals, preferably of 5 to 8 carbons, which have at least one bond including but not limited to cyclopentenyl, cyclohexenyl, and the like. The cycloalkenyl groups may be optionally substituted as herein defined.

For use herein the term "aryl" (on its own or in any combination, such as "arylalkyl" or "aryloxy") includes a single or fused ring system, suitably containing from 4 to 7, preferably 5 or 6 ring atoms in each ring, which rings, may each be unsubstituted or substituted by, independently for example, up to three substituents. A fused ring system may include an aliphatic ring, such as a saturated or partially saturated ring, and need include only one aromatic ring. Suitable aryl groups include phenyl and naphthyl such as 1-naphthyl or 2-naphthyl. The aryl rings may be optionally substituted as herein defined unless otherwise indicated.

For use herein the term "heterocyclyl" (on its own or in any combination, such as "heterocyclyl alkyl" or "heterocyclyl oxy") suitably includes, unless otherwise defined, non-aromatic, saturated or partially unsaturated, single and fused rings, suitably containing up to four heteroatoms in each ring, each of which independently selected from O, N and S or $S(O)_m$, and m is 0 or an integer having a value of 1 or 2, and which rings, may be unsubstituted or substituted independently by, for example, up to three substituents. Each heterocyclic ring suitably has from 4 to 7, preferably 5 or 6 ring atoms, or a fused ring system containing from 7 to 14 ring members. A fused heterocyclic ring system may include carbocyclic rings and need include only one heteroatom, as a heterocyclic ring. Examples of heterocyclyl groups include but are not limited to, the saturated or partially saturated versions of the heteroaryl moieties as defined herein, such as tetrahydropyrrole, tetrahydropyran, tetrahydrofuran, tetrahydrothiophene (including oxidized versions of the sulfur moiety), pyrrolidine, piperidine, piperazine, morpholine, thiomorpholine (including oxidized versions of the sulfur moiety), imidazolidine and pyrazolidine. The heterocyclic rings may be optionally substituted as herein defined below, unless otherwise indicated.

When used herein, the term "heteroaryl" (on its own or in any combination, such as "heteroaryloxy" or "heteroarylalkyl") suitably includes, unless otherwise defined, mono- and bicyclic heteroaromatic ring systems comprising up to four, preferably 1 or 2, heteroatoms each selected from O, N and S. Each ring may have from 4 to 7, preferably 5 or 6, ring atoms, or be a fused ring system containing from 8 to 12 ring members. A bicyclic heteroaromatic ring system may include a carbocyclic ring. Examples of heteroaryl groups include but are not limited to pyrrole, quinoline, isoquinoline, pyridine, pyrimidine, oxazole, thiazole, thiadiazole, triazole, imidazole, benzimidazole, isoxazole, thiophene, benzothiophene, furan, benzofuran, pyrazole, pyran, quinazolinyl, pyridazine, pyrazine, uracil, oxadiazole, oxathiadiazole, isothiazole, tetrazole, and indazole. The heteroaryl rings may be optionally substituted as defined herein below, unless otherwise indicated.

Suitably the when the term "optionally substituted" is used herein, such as on the alkyl, alkenyl, cycloalkyl, cycloalkenyl, aryl, arylalkyl, heterocyclyl, heterocyclicalkyl, heteroaryl, and heteroarylalkyl groups, unless otherwise defined, shall mean that the group may be optionally substituted one or more times, preferably by one to three substituents, each independently selected from halogen, $C_{1-6}$alkyl, aryl, aryl $C_{1-6}$alkyl, cycloalkyl, cycloalkyl $C_{1-6}$alkyl, $C_{1-6}$alkoxy $C_{1-6}$alkyl, halosubstituted $C_{1-6}$alkyl, aryl$C_{1-6}$alkoxy, $OR^{12}$, nitro, cyano, $(CR_{10}R_{20})_n$ $NR^{10}R^{11}$, $(CR_{10}R_{20})_n NR^{10}C(Z)R^{12}$, $(CR_{10}R_{20})_nC(Z)NR^{10}R^{11}$, $(CR_{10}R_{20})_nCOR^{12}$, $(CR_{10}R_{20})_n ZC(Z)R^{12}$, $(CR_{10}R_{20})_nC(Z)OR^{12}$, $(CR_{10}R_{20})_nC(O)NR^{10}R^{11}$, $(CR_{10}R_{20})_n NR^{10}C(Z)NR^{10}R^{11}$, $(CR_{10}R_{20})_n NR^{10}C(=NH)NR^{10}R^{11}$, $(CR_{10}R_{20})_n C(=NH)-NR^{10}R^{11}$, $(CR_{10}R_{20})_nNR^{10}S(O)_2R^8$, $(CR_{10}R_{20})_nS(O)_2NR^{10}R^{11}$, $S(O)_mR^{12}$, heterocyclyl, heteroaryl, heterocyclyl$C_{1-6}$alkyl or heteroaryl $C_{1-6}$alkyl. In addition, two adjacent ring carbon atoms may be linked to form a bicyclic system.

Particular compounds according to the invention include those mentioned in the examples and their pharmaceutically acceptable salts.

It will be appreciated that for use in medicine the salts of the compounds of formula (I) should be pharmaceutically acceptable. Suitable pharmaceutically acceptable salts will be apparent to those skilled in the art and include those described in *J. Pharm. Sci.*, 1977, 66, 1-19, such as acid addition salts formed with inorganic acids e.g. hydrochloric, hydrobromic, sulphuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention.

The compounds of this invention may be in crystalline or non-crystalline form, and, if crystalline, may optionally be hydrated or solvated. This invention includes within its scope stoichiometric hydrates as well as compounds containing variable amounts of water.

The invention extends to all isomeric forms including stereoisomers and geometric isomers of the compounds of formula (I) including enantiomers and mixtures thereof e.g. racemates. The different isomeric forms may be separated or resolved one from the other by conventional methods, or any given isomer may be obtained by conventional synthetic methods or by stereospecific or asymmetric syntheses.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

Compounds of Formula (I) are imidazole derivatives which may be readily prepared using procedures well-known to those skilled in the art, and described in, for instance, Comprehensive Heterocyclic Chemistry, Editors Katritzky and Rees, Pergamon Press, 1984, 5, 457-497, from starting materials which are either commercially available or can be prepared from such by analogy with well-known processes. A key step in many such syntheses is the formation of the central imidazole nucleus, to give compounds of formula (I). Suitable procedures are described in inter alia U.S. Pat. Nos. 3,707,475 and 3,940,486 which are herein incorporated by reference in their entirety. These patents describe the synthesis of a-diketones and α-hydroxyketones (benzoins) and their subsequent use in preparing imidazoles and N-hydroxylimidazoles. Thereafter, further compounds of formula (I) may be obtained by manipulating substituents in any of the groups $R^1$, $R^2$, and $R^3$ using conventional functional group interconversion procedures.

Scheme I

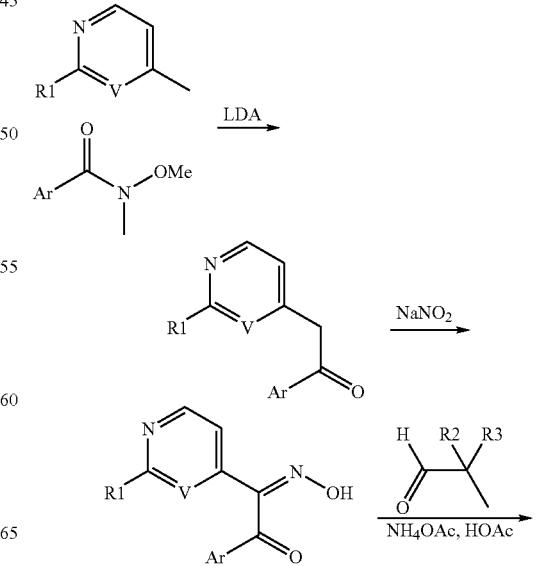

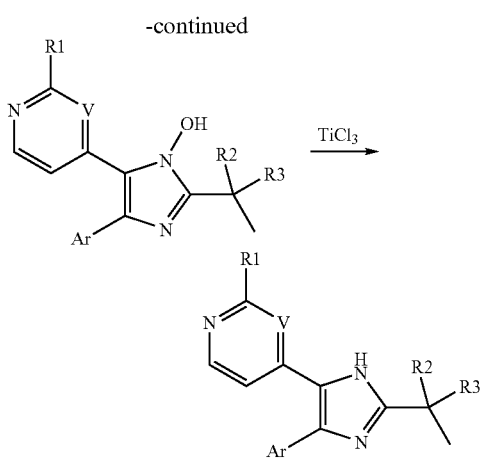

Compounds of the general formula I with Q=H can be prepared as outlined in Scheme I. Condensation of the anion of 4-methyl-2-(methylthio)pyrimidine with the Weinreb amide of an aryl acid will yield the ketone, which upon oxidation with sodium nitrite affords the ketooxime. Heating this product with an alkyl aldehyde and ammonium acetate in acetic acid allows access to the imidazole nucleus. Reduction of the hydroxyimidazole may be accomplished with heating with a trialkyl phosphite or stirring at ambient temperature with titanium trichloride. Replacement of the methylthio-group ($R^1$=SMe) with nucleophiles ($R^1$=$OR^4$, $NHR^4$, $SR^4$) can be effected by oxidation to the methylsulfinyl derivative with 3-chloroperoxybenzoic acid or oxone, followed by displacement with nucleophiles with or without the addition of bases such as sodium hydride, organolithiums or trialkylamines. In the case of amines ($R^1$=$NHR^4$), aluminum amide derivatives can be used to effect the displacements.

Scheme II

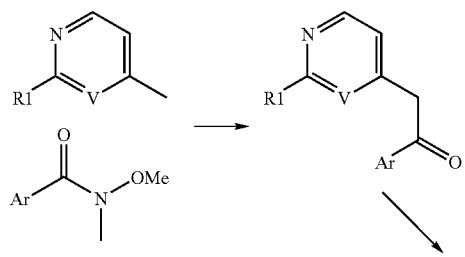

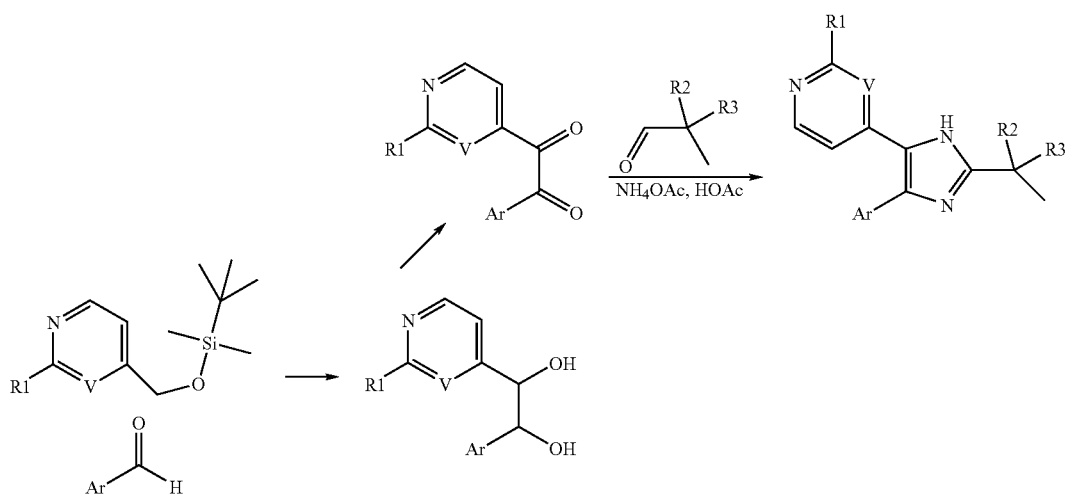

Alternative methods for preparing compounds of this invention are as outlined in the Scheme II. α-Diketones are prepared by condensation of the anion of, for example, a 4-substituted pyridine derivative (V=CH, $R^1$=H) with the Weinreb amide of an aryl acid or an aryl-aldehyde, followed by oxidation of the intermediate product. Heating the diketone with an aldehyde and ammonium acetate in acetic acid allows access to the imidazole nucleus.

Compounds of the general formula ($R^1$=$OR^4$, $NHR^4$, $SR^4$) can be prepared as in Schemes I or II except substituting 4-methyl-2-chloropyridine or 4-methyl-2-fluoropyridine for 4-methylpyridine (Gallagher et al *Bioorg. Med. Chem.* 5, 49, 1997). Nucleophilic substitution of the resulting 2-halopyridinylimidazole can be effected by the procedure described in U.S. Pat. No. 5,670,527.

Alternatively compounds may be prepared as in Scheme III wherein the Aryl (Ar) group is added last.

Scheme III

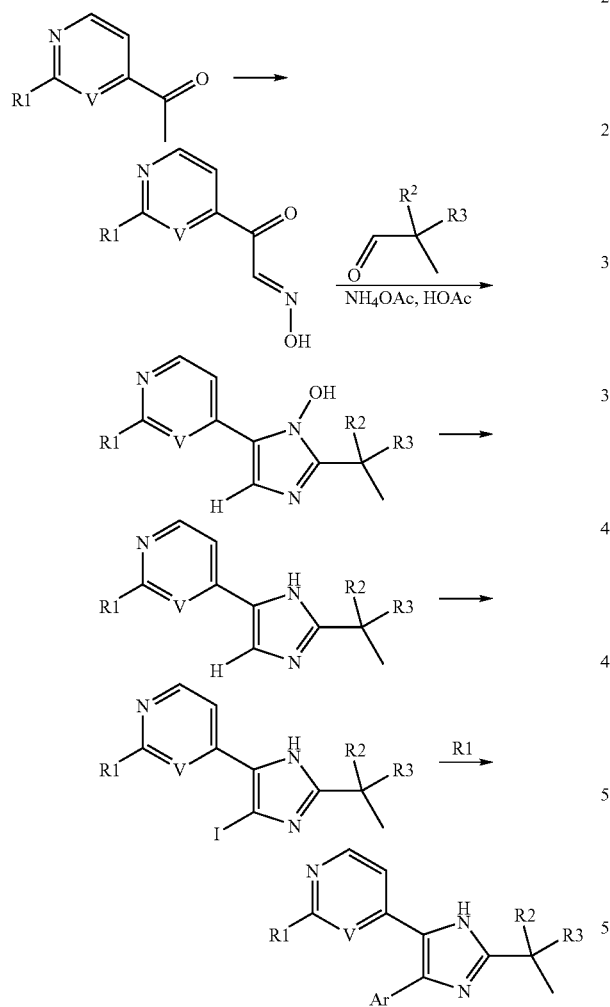

Oxidation of a 4-acetyl substituted pyridine derivative (V=CH, $R^1$=H) with sodium nitrite affords the ketooxime. Heating this product with an alkyl aldehyde and ammonium acetate in acetic acid allows access to the imidazole nucleus. Reduction of the hydroxyimidazole may be accomplished with heating with a trialkyl phosphite or stirring at ambient temperature with titanium trichloride. Treatment of the imidazole with N-iodosuccinimide gives the iodoimidazole with then may be reacted with various boronic acids under palladium catalysis to give the aryl or heteroaryl imidazoles. Alternative biaryl coupling reactions may also be used.

The synthetic schemes described above afford a compound of Formula I with Q=H. Alkylation of this intermediate with an alkyl halide (Cl, Br, I or F) or other reactive alkylating agent (for example, an sulfonate ester, such as mesylate or tosylate) in the presence of an appropriate base and solvent and affords compounds of Formula I in which Q now fits the generally outlined structural requirements outlined or compounds of this invention. Alternatively, biaryl coupling chemistry may be employed to prepare Q is a directly attached aryl, heteroaryl, alkenyl or alkynyl. Such chemistry is well known to those skilled in the art and has been reported for coupling to heterocyclic nitrogens, such as those in imidazole. It should be appreciated that both the alkylation and coupling reactions may also give rise to variable amounts of the undesired regioisomers, from which the desired product may be obtained using any number of standard separation techniques, including chromatography and crystallisation. By variation of the alkylation conditions and dependent on the particular structure of both reactants, the ratio of desired formula I to undesired products may be greatly influenced. Examples of generally effective conditions for the alkylation reaction and conditions which favor the production of the regioisomer of Formula I are presented in Liverton, et. al., *J. Med. Chem. Vol.* 42, No. 12, p2180-2190, 1999.

Regioselective placement of Q in compounds of Formula (I) is possible as illustrated in Scheme IV. Addition of a primary amine to the aldehyde prior to addition of the ketooxime results in selective N-Q formation adjacent to the Aryl ring of the hydroxyimidazole. Reduction as in Scheme III with trialkyl phosphite or titanium trichloride affords compounds of Formula (I).

Scheme IV

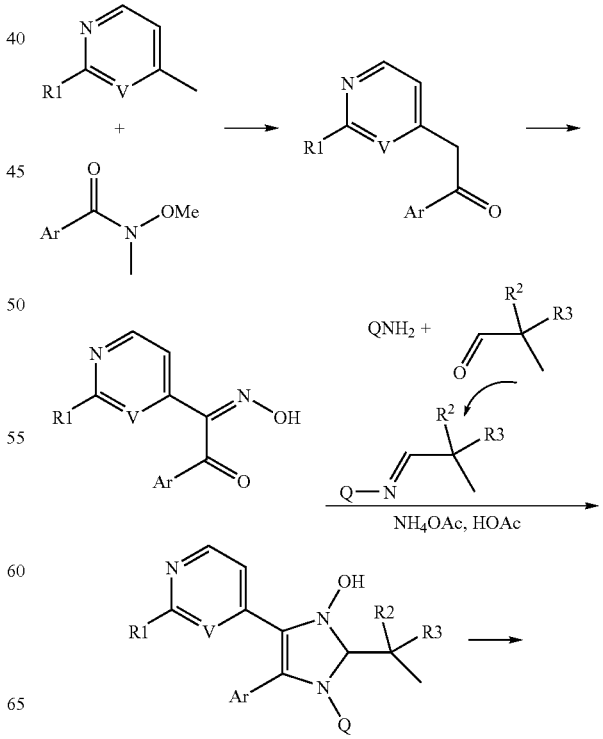

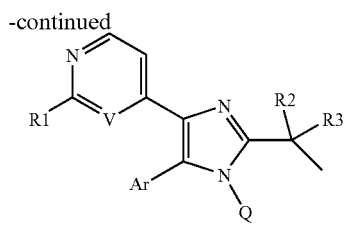

Suitable protecting groups for use with hydroxyl groups and the imidazole nitrogen are well known in the art and described in many references, for instance, Protecting Groups in Organic Synthesis, Greene T W, Wiley-Interscience, New York, 1981. Suitable examples of hydroxylprotecting groups include silyl ethers, such as t-butyldimethyl or t-butyldiphenyl, and alkyl ethers, such as methyl connected by an alkyl chain of variable link, $(CR^{13}R^{14})_n$. Suitable examples of imidazole nitrogen protecting groups include tetrahydropyranyl.

SYNTHETIC EXAMPLES

The invention will now be described by reference to the following examples which are merely illustrative and are not to be construed as a limitation of the scope of the present invention.

All temperatures are given in degrees centigrade (° C.), all solvents are highest available purity and all reactions run under anhydrous conditions in an argon atmosphere unless otherwise indicated. Mass spectra were performed upon a VG Zab mass spectrometer using fast atom bombardment or on a micromass platform electrospray ionization mass spectrometer in the positive ion mode using 95:5 $CH_3CN/CH_3OH$ with 1% formic acid as the carrier solvent, unless otherwise indicated. $^1$H-NMR (hereinafter "NMR") spectra were recorded at 250 MHz or 400 Mz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant. Flash chromatography is run over Merck Silica gel 60 (230-400 mesh).

Example 1

Preparation of 2-tert-Butyl-4-naphthalen-2-yl-5-pyridin-4-yl-imidazole

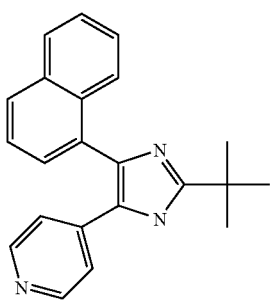

a) 2-Oxo-2-pyridin-4-yl-acetaldehyde oxime

Isoamyl nitrite (11,7 grams (hereinafter "g"), 0.1 millimoles (hereinafter "mmol")) was added to alkaline ethanol [NaOH (4 g) in EtOH (50 milliliters (hereinafter "ml"))] followed by cooling to 0° and addition dropwise addition of 4-acetylpyridine (12.1 g in 95% ethanol 10 ml) with vigorous stirring. After complete addition the reaction was placed in the refrigerator overnight. The mixture was diluted with ether and filtered to give a light reddish-brown solid. This was dissolved in water and at 0° acidified to pH 5.0 with glacial HOAc to give an orange solid 6.76 g. The solid was recrystallized from 30/70 EtOH/$H_2O$ to give 2-Oxo-2-pyridin-4-yl-acetaldehyde oxime as needles (5.0 g 33%). $^1$H NMR(400 MHz, $CDCl_3$) δ 8.61(dd, J=4.6 Hz, 1.422H), 7.85 (s, 1H), 7.80(dd, J=4.6, 1.5 Hz, 2H).

b) 2-tert-Butyl-5-pyridin-4-yl-imidazol-1-ol

A solution of 2-Oxo-2-pyridin-4-yl-acetaldehyde oxime (9.87 g, 65.8 mmol), trimethylacetaldehyde (6.8 g, 79 mmol), and ammonium acetate (50.7 g) in glacial acetic acid (600 ml) was kept at 87° for 4 h, then at 80° for 4 h after the addition of trimethyl acetaldehyde (1 ml). The yellow solution was cooled to 0° and carefully neutralized with conc. ammonium hydroxide with vigorous stirring. At pH 7.0-7.2 a copious precipitate formed and the mixture was stirred for 30 min. The beige solid was filtered off and dried in a vacuum oven at 400 to yield the title compound (11.0 g). The aqueous filtrate was further extracted with $CH_2Cl_2$ to give an additional yellow oil (3.12 g) as a mixture of title compound and corresponding imidazole.

c) 4-(2-tert-Butyl-1-H-imidazol-4-yl)-pyridine

The compound in Example 1 (b) was treated with trimethyl phosphite (25 ml) in DMF (200 ml) and kept at 90° for 3 hr. The DMF was distilled off under reduced pressure and the residue partitioned between water (pH 8) and chloroform and extracted several times into chloroform. The organic portions were dried over $MgSO_4$ and evaporated then triturated with ether to give the title compound. (9.33 g) $^1$H NMR(400 MHz, $CDCl_3$) δ 9.35(br s, 1H), 8.56(d, J=5.6 Hz, 2H), 7.68 (d, J=4.9, 2H) 7.38 (s, 2H), 1.44 (s, 9H).

d) 4-(2-tert-Butyl-5-iodo-3-H-imidazol-4-yl)-pyridine

The compound in Example 1(c) (3.)g, 14.92 mmol in EtOH (60 ml) was treated with N-iodosuccinimide at room temperature (hereinafter "rt") for 4 hours (hereinafter "h"). Thin layer chromatography (Tlc) showed complete reaction and the mixture was diluted with water slowly. The resultant solid was filtered and dried under high vacuum overnight at 60° to afford the title compound. (4.39 g, 90%) MS m/e: 328 $[M+H]^+$, 326 $[M-H]^-$;

e) 2-tert-Butyl-4-naphthalen-2-yl-5-pyridin-4-yl-imidazole

In a heavy-walled pressure vessel 4-(2-tert-Butyl-5-iodo-3-H-imidazol-4-yl)-pyridine (100 milligrams (hereinafter "mg"), 0.3 mmol) and tetrakis-triphenylphosphine palladium (0) catalyst was dissolved in toluene (2-3 ml) and argon was bubbled through the solution while the other reagents were added: 1-naphthyl boronic acid (86 mg, 0.5 mmol), solid $NaHCO_3$ (84 mg), water (500 uL), EtOH (500 uL). The vessel was sealed and the reaction heated to 100° overnight. The reaction mixture was partitioned between 5% $NaHCO_3$ and EtOAc and extracted several times with EtOAc. The combined organic layers were washed with brine, dried over MgSO₄, filtered, and evaporated. The crude product was chromatographed on silica gel (chromatotron, eluting with 1-4% MeOH/CH₂Cl₂) to give the title compound as a yellow solid. (58 mg, 59%). mp 218-220°; MS m/e: 328 [M+H]⁺, 326 [M−H]⁻; ¹H NMR(400 MHz, CDCl₃) δ 9.63(br s, 1H), 8.16 (app d, J=4.8 Hz, 2H), 7.92(br d, J=8.3 Hz, 2H), 7.64 (br d, 1H), 7.52 (m, 3H), 7.41 (t, J=6 Hz, 1H), 7.29 (br s, 2H), 1.49 (s, 9H).

Example 2

Preparation of 2-tert-Butyl-4-(6-Ethoxynaphthalen-2-yl)-5-pyridin-4-yl-imidazole

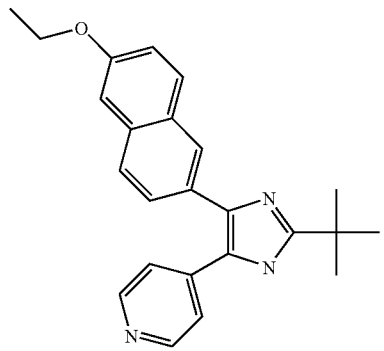

a) 2-Bromo-6-ethoxy-naphthalene

To a suspension of sodium hydride (800 mg, 60% oil dispersion) in DMF (20 ml) was added a solution of 6-Bromo-2-naphthol dropwise with stirring at 0°. After gas evolution had ceased, neat ethyl iodide (1.6 ml) was added dropwise to the stirred solution. The reaction was stirred overnight at rt. The reaction mixture was poured into water and extracted several times with tert-butyl methyl ether. The combined organic extracts were washed with water and brine, then dried over MgSO₄, filtered and evaporated under reduced pressure to give tan solid. This was recrystallized from MeOH and dried under high vacuum to a constant wt. giving a white solid (3.11 g, 60%). ¹H NMR(400 MHz, CDCl₃) δ 7.92 (d, J=1.7 Hz, 1H), 7.65(d, J=8.9 Hz, 1H), 7.59 (d, J=8.7 Hz, 2H), 7.16 (dd, J=8.9 Hz, 2.48, 1H), 7.09 (d, J=2.4 Hz, 1H), 4.15 (q, 2H), 1.49 (t, 3H).

b) 6-Ethoxy-naphth-2-yl boronic acid

To a solution of Example 2(a) (2.51 g, 10 mmol) in dry THF (15 ml, freshly distilled from Na) at −78° C. was added dropwise 2.5 M n-butyl lithium (4 ml, 10 mmol) over ~5 min. The reaction was stirred at −78° C. for 10 min then triisopropyl borate (3.46 ml) was added and the reaction was allowed to come to rt. The reaction was partitioned between 10% ammonium chloride and tert-butyl methyl ether and further extracted with and tert-butyl methyl ether (×3), washed with brine, dried with MgSO₄ and evaporated to a white solid. The solid was triturated with hot hexanes to give pure title compound. (1.9 g, 88%) MS(ES) m/e: 217 [M+H]⁺.

c) 2-tert-Butyl-4-(6-Ethoxynaphthalen-2-yl)-5-pyridin-4-yl-imidazole

Following the procedure of Example 1(e), except substituting 6-Ethoxy-naphth-2-yl boronic acid for 1-naphthyl boronic acid the title compound was prepared. (34 mg, 34%) mp 258-259°; MS m/e: 372 [M+H]⁺, 370 [M−H]⁻;

Example 3

Preparation of 4-(2-tert-butyl-5-(6-methoxy-napthalen-2-yl)-3H-imadazol-4-yl)-pyridine

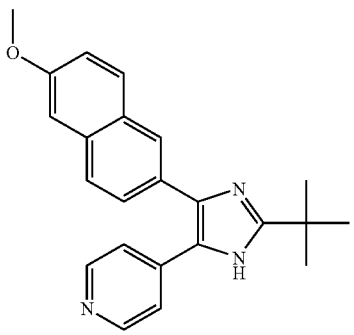

a) 6-Methoxy-2-naphthoic-N-methoxy-N-methyl amide

At 0° C., SOCl₂ (1.15 mL, 15.8 mmol) was added very slowly to a stirred solution of 6-methoxy-2-naphthoic acid (2.9 g, 14.3 mmol) in CH₂Cl₂ (40 mL) and Et₃N (7.9 mL, 57.2 mmol). The solution became dark and homogeneous. After stirring at room temperature for 40 min., N, O-dimethylhydroxylamine hydrochloride (1.86 g, 17.16 mmol) was added. After the reaction was stirred for 2 h, it was quenched with water, then extracted with CH₂Cl₂ (3×). The organic layer was washed with saturated Na₂CO₃(3×), dried (Na₂SO₄), concentrated to afford 6-methoxy-2-naphthoic-N-methoxy-N-methyl amide. (3.65 g, 94%) MS(ES) m/e 246 [M+H]⁺.

b) 6-Methoxynaphth-2-yl-4-pyridylmethyl ketone

At 0° C., n-BuLi (2.5 M in hexane, 8.12 mL, 20.3 mmol) was added to a solution of diisopropylamine (3.32 mL, 23.6 mmol) in THF (20 mL) to generate LDA. The solution was cooled to −78° C., 4-picoline (2.00 mL, 20.3 mmol) was added to the solution, the solution was kept at −78° C., and stirred for 15 min, then compound in Example 3(a) (3.65 g, 14.9 mmol) was added. The reaction was warmed to rt over 0.5 h, and stirred for another 1 h. The reaction was quenched by NH₄Cl (5 mL), extracted with CH₂Cl₂ (3×). The organic layer was washed with brine, dried (MgSO₄), and concentrated. The obtained residue was subjected to flash column (from 1% MeOH in CH₂Cl₂ to 4% MeOH in CH₂Cl₂) to afford 6-methoxynaphth-2-yl-4-pyridylmethyl ketone. (3.3 g, 70%) MS(ES) m/e 278 [M+H]⁺.

c) 2-Hydroxyimino-1-(6-methoxynaphth-2-yl)-2-(4-pyridyl)ethan-1-one

NaNO$_2$ (0.9 g, 14.3 mmol) was added to a suspension of compound in Example 3(b) (3.3 g, 11.9 mmol) in 3N HCl (70 mL), and H$_2$O (70 mL). The slurry was stirred for 3 h, filtered, washed with water, air dried to give 2-hydroxyimino-1-(6-methoxynaphth-2-yl)-2-(4-pyridyl)ethan-1-one. (3.4 g, 93%) MS(ES) m/e 307 [M+H]$^+$.

d) 4-(2-tert-Butyl-5-(6-methoxy-napthalen-2-yl)-5-pyridin-4-yl)-imidazol-1-ol Acetic acid (3 mL) was added to a mixture of trimethylacetaldehyde (21 μL, 1.37 mmol), ammonium acetate (125 mg, 1.6 mmol), and compound in Example 3(c) (50 mg, 0.16 mmol). After the resulting solution was heated at 110° C. overnight, it was cooled to 0° C., then NH$_4$OH was added to the solution slowly with stirring. The precipitate formed was filtered, and dried to afford 4-(2-tert-butyl-5-(6-methoxy-napthalen-2-yl)-5-pyridin-4-yl)-imidazol-1-ol. (35 mg, 57%) MS(ES) m/e 375 [M+H]$^+$.

e) 4-(2-tert-Butyl-5-(6-methoxy-napthalen-2-yl)-3H-imidazol-4-yl)-pyridine

Triethylphosphite (63 mg, 0.4 mmol) was added to a stirred solution of the compound in Example 3(d) (50 mg, 0.13 mmol) and N,N-dimethylformamide (2 mL) at room temperature. The reaction was stirred for 8 hours. Then excess water was added and the mixture stirred for 3 hours. The solid precipitate was filtered and dried under vacuum to afford the title compound. (27 mg, 57%) MS(ES) m/e 358 [M+H]$^+$.

Example 4

Preparation of 2-tert-Butyl-4-Inden-2-yl)-5-pyridin-4-yl-1H-imidazole

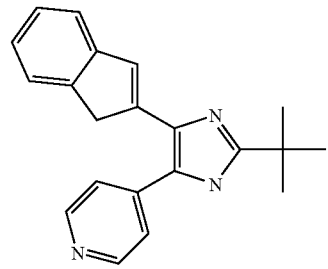

2-tert-Butyl-4-Inden-2-yl)-5-pyridin-4-yl-1H-imidazole trifluoracetate salt

A mixture of indene (175 uL, 1.5 mmol), tetrabutylammonium chloride (83 mg, 0.3 mmol), palladium acetate (3 mg), tri-o-tolylphosphine (6 mg), and the compound in Example 1(d) (100 mg, 0.3 mmol) in DMF (1 ml) were microwaved for 10 min at 30 W and for 24 min at 45W. Both tlc and lc/ms were indicative of complete reaction. The mixture was partitioned between CH$_2$Cl$_2$ and 5% NaHCO$_3$. The aqueous layer was extracted with CH$_2$Cl$_2$ (×4), washed with H$_2$O, dried (MgSO$_4$), and concentrated. The crude product was chromatographed on silica gel (chromatotron, from 1% MeOH in CH$_2$Cl$_2$ to 4% MeOH in CH$_2$Cl$_2$) to afford title compound (27 mg) contaminated with tetrabutylammonium chloride. Preparative hplc (YMS-combiprep ODS-A, 20-80% acetonitrile/water 0.1% TFA) afforded pure title compound as a bright yellow solid (9.2 mg, 10%). MS(ES) m/e 358 [M+H]$^+$, 370 [M–H]$^-$, 350 [M+Cl–H]$^-$, 442 [M+I–H]$^-$.

Example 5

2-tert-Butyl-4-Benzofuran-2-yl-5-pyridin-4-yl-1H-imidazole

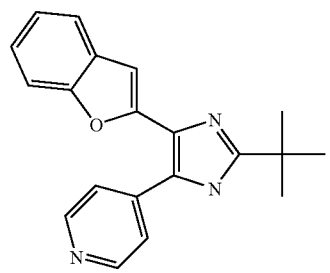

Following the procedure of Example 1(e), except substituting Benzofuran-2-boronic acid for 1-naphthyl boronic acid and Na$_2$CO$_3$ for NaHCO$_3$, the title compound was prepared by microwave for 16 min at 45W. (34 mg, 66%) MS(ES) m/e 318 [M+H]$^+$, 316 [M–H]$^-$.

Example 6

4-(2-tert-Butyl-5-dibenzothiophen-4-yl-1H-imidazol-4-yl)-pyridine

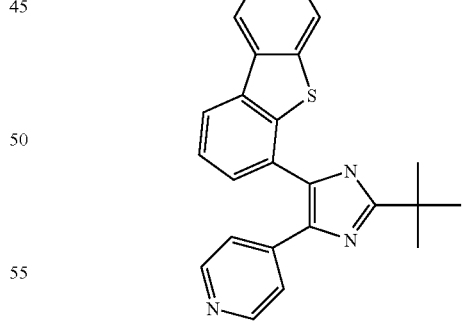

Following the procedure of Example 1(e), except substituting Dibenzothiaphene-4-boronic acid for 1-naphthyl boronic acid and Na$_2$CO$_3$ for NaHCO$_3$, the title compound was prepared in a 96 well-plate format with microwave for 2 hr at 100-200W with temperature not exceeding 65°. Purified by hplc (YMS-combiprep ODS-A, 20-80% acetonitrile/water 0.1% TFA (6 mg, 10%) Lc-MS(ES) m/e 384 [M+H]$^+$, 97%.

Example 7

4-(2-tert-Butyl-5-dibenzofuran-4-yl-1H-imidazol-4-yl)-pyridine

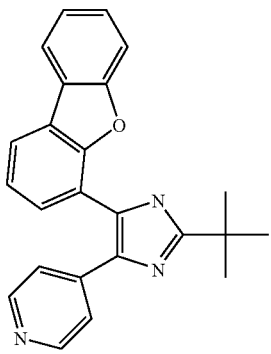

Following the procedure of Example 1(e), except substituting Dibenzofuran-4-boronic acid for 1-naphthyl boronic acid and Na₂CO₃ for NaHCO₃, the title compound was prepared in a 96 well-plate format with microwave for 2 hr at 100-200W with temperature not exceeding 65°. Purified by hplc (YMS-combiprep ODS-A, 20-80% acetonitrile/water 0.1% TFA (9 mg, 16%) Lc-MS(ES) m/e 368 [M+H]⁺, 100%

Example 8

4-(5-Benzo[b]thiophen-2-yl-2-tert-butyl-1H-imidazol-4-yl)-pyridine

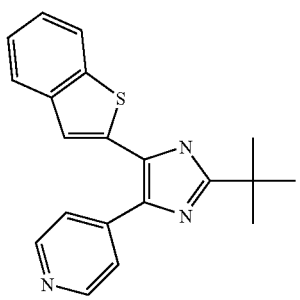

Following the procedure of Example 1(e), except substituting thiaphene-2-boronic acid for 1-naphthyl boronic acid and Na₂CO₃ for NaHCO₃, the title compound was prepared in a 96 well-plate format with microwave for 2 hr at 100-200 W with temperature not exceeding 65°. Purified by hplc (YMS-combiprep ODS-A, 20-80% acetonitrile/water 0.1% TFA (34 mg, 64%) Lc-MS(ES) m/e 334 [M+H]⁺, 100%

Example 9

4-(5-Benzo[b]thiophen-3-yl-2-tert-butyl-1H-imidazol-4-yl)-pyridine

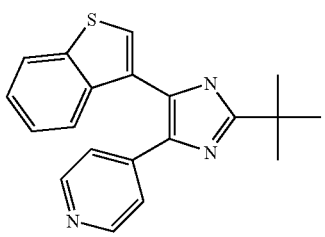

Following the procedure of Example 1(e), except substituting thiaphene-3-boronic acid for 1-naphthyl boronic acid and Na₂CO₃ for NaHCO₃, the title compound was prepared in a 96 well-plate format with microwave for 2 hr at 100-200 W with temperature not exceeding 65°. Purified by hplc (YMS-combiprep ODS-A, 20-80% acetonitrile/water 0.1% TFA (5 mg, 8%) Lc-MS(ES) m/e 334 [M+H]⁺, 100%.

Example 10

4-(2-tert-Butyl-5-thianthren-1-yl-1H-imidazol-4-yl)-pyridine

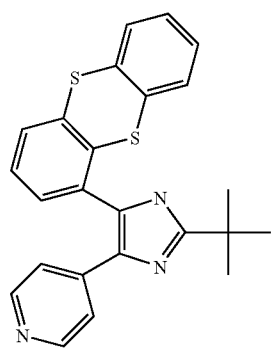

Following the procedure of Example 1(e), except substituting thianthrene-1-boronic acid for 1-naphthyl boronic acid and Na₂CO₃ for NaHCO₃, the title compound was prepared in a 96 well-plate format with microwave for 2 hr at 100-200W with temperature not exceeding 65°. Purified by hplc (YMS-combiprep ODS-A, 20-80% acetonitrile/water 0.1% TFA (3 mg, 5%) Lc-MS(ES) m/e 416 [M+H]⁺, 100%.

Example 11

4-(2-tert-Butyl-5-phenoxathin-4-yl-1H-imidazol-4-yl)-pyridine

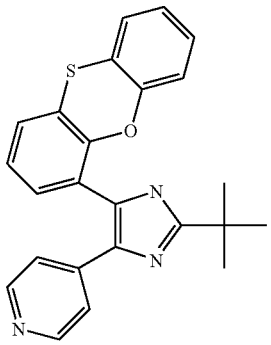

Following the procedure of Example 1(e), except substituting 4-phenoxathine boronic acid for 1-naphthyl boronic acid and Na₂CO₃ for NaHCO₃, the title compound was prepared in a 96 well-plate format with microwave for 2 hr at 100-200W with temperature not exceeding 65°. Purified by hplc (YMS-combiprep ODS-A, 20-80% acetonitrile/water 0.1% TFA (4 mg, 6%) Lc-MS(ES) m/e 400 [M+H]⁺, 93%.

Example 12

4-[2-tert-Butyl-5-(6-methoxy-naphthalen-2-yl)-1-methyl-1H-imidazol-4-yl]-pyridine

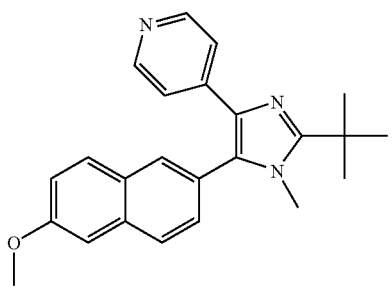

Methylamine (2 mL of a 1M solution in methanol) was added to an acetic acid solution (2 ml) of trimethylacetaldehyde (353 μL, 3.2 mmol). After stirring at room temperature for 1 hour, the keto-oxime was added (200 mg, 0.65 mmol). The resulting solution was heated at 80° C. for 24 hours. The reaction was allowed to cool to room temperature, then the solution was neutralized with NH$_4$OH. The reaction mixture was extracted with methylene chloride and the combined organics were dried over anhydrous magnesium sulfate.

The crude product was dissolved in 5 mL of methanol and 1 mL of TiCl$_3$ (>10% in HCl) was added. The reaction was stirred at room temperature for 18 hrs. The methanol was removed under reduced pressure and the slurry was diluted with water. The pH was adjusted to 8 with the addition of NH$_4$OH, and the solution was extracted with EtOAc. The combined organic extracts were dried over MgSO$_4$, filtered and concentrated. The crude product was purified via flash chromatography (silica gel, 5% methanol/methylene chloride) to afford 75 mg (0.2 mmol, 31% yield); $^1$H NMR (400 MHz, CDCl$_3$) δ 8.25 (d, 2H), 7.80 (d, 1H), 7.70 (s, 1H), 7.65 (d, 1H), 7.25 (d, 1H), 7.10 (m, 4H), 3.90 (s, 3H), 3.10 (s, 3H), 0.20 (s, 3H); MS (ES) 372 [M+H]$^+$.

Example 13

4-[2-tert-Butyl-5-(6-methoxy-naphthalen-2-yl)-3-H-imidazol-4-yl]-pyridin-2-yl}-(3-morpholin-4-yl-propyl)-amine

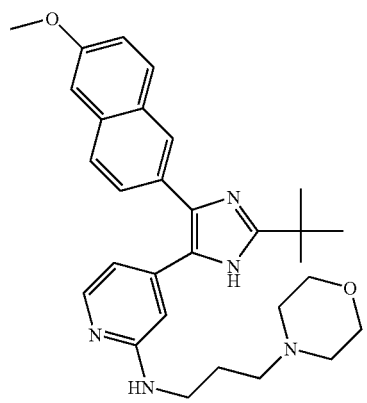

a) 6-Methoxynaphth-2-yl-(2-fluoropyridin-4-yl)-methyl ketone

At 0° C., n-BuLi (2.5 M in hexane, 19.6 mL, 48.92 mmol) was added to a solution of diisopropylamine (8.0 mL, 57.08 mmol) in THF (60 mL) to generate LDA. After 15 min stirring at 0° C., the solution was cooled to −78° C. and 2-fluoropicoline (5.44 mL, 48.92 mmol) in THF (30 ml) was added to the solution. The solution was kept at −78° C., and stirred for 30 min, then compound in Example 3(a) (10.0 g, 40.77 mmol) was added. The reaction was warmed to room temperature (hereinafter "rt") over 0.5 h, and stirred for another 40 min. The reaction was quenched by KHPO$_4$ (0.5 M), extracted with EtOAc (3×). The organic layer was washed with brine, dried (MgSO$_4$), and concentrated then pumped under high vacuum to afford 6-methoxynaphth-2-yl-4-pyridylmethyl ketone as pale yellow solid. (11.82 g, 98%) MS(ES) m/e 296 [M+H]$^+$.

b) 2-Hydroxyimino-1-(6-methoxynaphth-2-yl)-2-(2-fluoropyridin-4-yl)ethan-1-one At 0° C., t-butylnitrite (3.46 mL, 28.5 mmol) was added dropwise to a solution of Example x(1) (8.0 g, 27.1 mmol) in THF (400 mL) under Argon. After 3 min stirring at 0° C., an HCl solution (2M in ether, 32.0 mL, approx. 64 mmol) was added dropwise to the solution. The solution was kept at rt for 2 h, then the solvent was removed under reduced pressure and the brown oily residue was partitioned between water and CH$_2$Cl$_2$ after adjusting the pH to 8, extracted further with CH$_2$Cl, washed with brine, dried (MgSO$_4$), and concentrated then pumped under high vacuum overnight to afford on oil which was recrystallized from t-butyl-O-methyl ether/hexane to give as an orange solid 2-hydroxyimino-1-(6-methoxynaphth-2-yl)-2-(2-fluoropyridin-4-yl)ethan-1-one. (7.66 g, 87%) MS(ES) m/e 325 [M+H]$^+$.

c) {4-[2-tert-Butyl-5-(6-methoxy-naphthalen-2-yl)-3-H-imidazol-4-yl]-pyridin-2-yl}-(3-morpholin-4-yl-propyl)-amine A mixture of trimethylacetaldehyde (60 μL, 0.55 mmol), ammonium trifluoroacetate (500 mg), N-(3-aminopropyl)morpholine (200 μL, >1.2 mmol) and compound in Example 2(x) (130 mg, 0.40 mmol) was heated as a melt at 150° C. for several hours. After cooling to rt, the reaction mixture was dissolved in water and extracted with EtOAc (3×). The combined extracts were concentrated and redissolved in DMSO and purified by hplc to afford after lyopholization pure {4-[2-tert-Butyl-5-(6-methoxy-naphthalen-2-yl)-3-H-imidazol-4-yl]-pyridin-2-yl}-(3-morpholin-4-yl-propyl)-amine. (68.4 mg, 57%) MS(ES) m/e 500 [M+H]$^+$ 100%.

Example 14

{4-[2-tert-Butyl-5-(6-methoxy-naphthalen-2-yl)-3-H-imidazol-4-yl]-pyridin-2-yl}-(3-morpholin-4-yl-ethyl)-amine

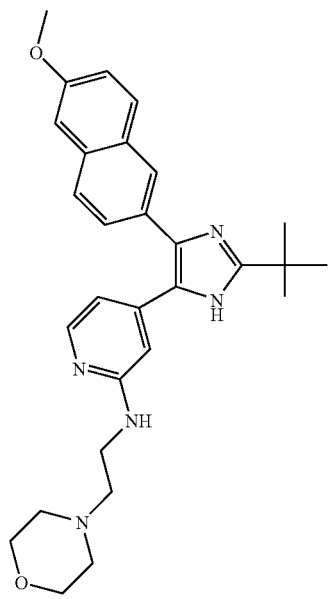

Following the procedure of Example 13(c), except substituting N-(3-aminoethyl)morpholine for N-(3-aminopropyl)morpholine, the title compound was prepared. (124 mg, 43%) Lc-MS(ES) m/e 486 [M+H]$^+$, 100% uv, 100% els.

Example 15

{4-[2-tert-Butyl-5-(6-methoxy-naphthalen-2-yl)-3-H-imidazol-4-yl]-pyridin-2-ylamino}-propyl)-pyrrolidin-2-one

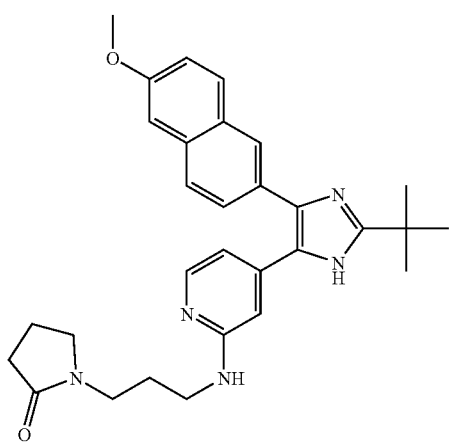

Following the procedure of Example 13(c), except substituting N-(3'-aminopropyl)-2-pyrrolidinone for N-(3-aminopropyl)morpholine, the title compound was prepared. (99.1 mg, 41%) Lc-MS(ES) m/e 498 [M+H]$^+$, 89% uv, 100% els.

Example 16

{4-[2-tert-Butyl-5-(6-methoxy-naphthalen-2-yl)-3-H-imidazol-4-yl]-pyridin-2-yl}-[3-(2-methyl-piperidin-1-yl)-propyl]-amine

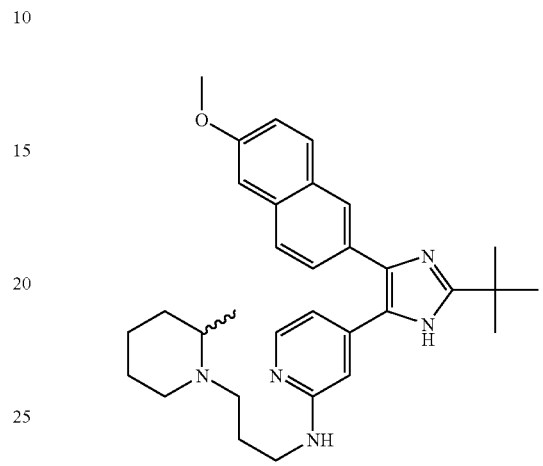

Following the procedure of Example 13(c), except substituting 1-(3-aminopropyl)-2-pipecoline for N-(3-aminopropyl)morpholine, the title compound was prepared. (57.1 mg, 23%) Lc-MS(ES) m/e 512 [M+H]$^+$, 96% uv, 100% els.

Example 17

{4-[2-tert-Butyl-5-(6-methoxy-naphthalen-2-yl)-3-H-imidazol-4-yl]-pyridin-2-yl}-N,N-diethyl-butane-1,4-diamine

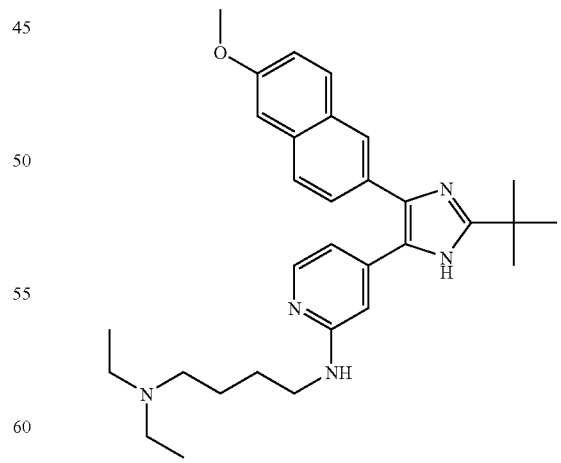

Following the procedure of Example 13(c), except substituting 4-(diethylamino)butylamine for N-(3-aminopropyl)morpholine, the title compound was prepared. (51.4 mg, 21%) Lc-MS(ES) m/e 500 [M+H]$^+$, 91% uv, 100% els.

Example 18

{4-[2-tert-Butyl-5-(6-methoxy-naphthalen-2-yl)-3-H-imidazol-4-yl]-pyridin-2-yl}-(3-pyrrolidin-1-yl-propyl)-amine

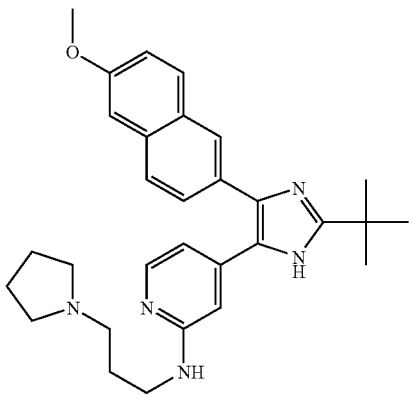

Following the procedure of Example 13(c), except substituting n-(2-aminopropyl)pyrrolidine for N-(3-aminopropyl)morpholine, the title compound was prepared. (10.2 mg, 4%) Lc-MS(ES) m/e 484 [M+H]+, 100% uv, 100% els.

Example 19

{4-[2-tert-Butyl-5-(6-methoxy-naphthalen-2-yl)-3-H-imidazol-4-yl]-pyridin-2-yl}-[3-(4-methyl-piperazin-1-yl)-propyl]-amine

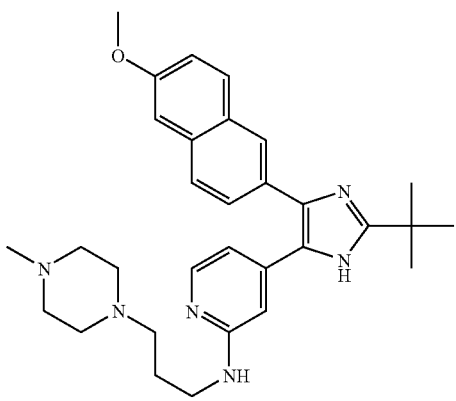

Following the procedure of Example 13(c), except substituting 1-(3-aminopropyl)-4-methylpiperazine for N-(3-aminopropyl)morpholine, the title compound was prepared. (54.1 mg, 22%) Lc-MS(ES) m/e 513 [M+H]+, 100% uv, 100% els

Example 20

{4-[2-tert-Butyl-5-(6-methoxy-naphthalen-2-yl)-3-H-imidazol-4-yl]-pyridin-2-yl}-N,N-diethyl-ethane-1,2-diamine

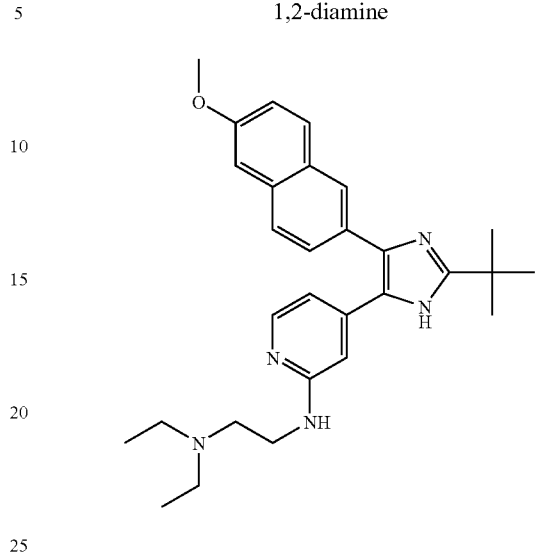

Following the procedure of Example 13(c), except substituting N,N-diethylethylenediamine for N-(3-aminopropyl)morpholine, the title compound was prepared. (23.2 mg, 10%) Lc-MS(ES) m/e 472 [M+H]+, 89% uv, 100% els Methods of Treatment The Tie receptors are proteins of approximately 125 kDa, with a single putative transmembrane region. The extracellular domain of these receptors is divided into several regions: there are 3 regions that have a pattern of cysteine expression found in EGF-like domains; there are 2 regions that have some weak homology to and structural characteristics of immunoglobulin-like domains; and there are 3 regions with homology to the fibronectin III repeat structure. This particular combination of extracellular domains is unique to the Tie receptors. The intracellular portion of Tie2 is most closely related (~40% identity) to the kinase domains of FGF-R1, PDGF-R and c-kit. The intracellular portions of Tie2 contain all of the features of tyrosine kinases, including a GXGXXG ATP binding site consensus sequence and typical tyrosine kinase motifs (i.e., HRDLAARN and DFGL).

These receptors have sparked interest because they are the only receptor tyrosine kinases, other than those receptors for vascular endothelial cell growth factor (VEGF), that are largely restricted to endothelial cells in their expression. There are several lines of evidence showing that Tie2 is important in angiogenesis, detailed in the following paragraphs.

a. Tie1 and Tie2 Receptor Location i. Embryological Vascular Development

The location of the Tie receptors in the embryo has been studied by a number of investigators using in situ hybridization. Korhonen et al. (*Blood* 80:2548-2555, 1992) showed that the mRNA for Tie receptors is located in endothelial cells of all forming blood vessels and in the endocardium of mouse embryos. During embryonic development, expression of the Tie receptors is seen in angioblasts and all developing vasculature. Expression of the Tie receptors follows expression of the major VEGF receptor, Flk-1, by 12-24 hours during mouse embryogenesis, perhaps suggesting sequential and different actions of these receptor systems (Schnurch and Risau, *Development* 119: 957-968, 1993). Cloning of a 1.2

Kb genomic 5' flanking region of Tie2, coupled to a lacZ gene and expressed in transgenic mice, demonstrated a selective pattern of expression in endothelial cells during embryonic development (Schlaeger et al., *Development* 121:1089-1098, 1995). Thus, the Tie2 promoter acts to assure endothelial cell-specific expression of Tie2.

ii. In Adult Tissues

The similarities between embryonic angiogenesis and pathologic angiogenesis yields the hypothesis that blocking Tie2 function, in tumors or chronic inflammatory settings, for examples, may block angiogenesis, thus blocking further cell proliferation and provide therapeutic benefit. Tie mRNA cannot be observed in adult skin, except at sites of active wound healing, where the proliferating capillaries in the granulation tissue contain abundant Tie mRNA (Korhonen et al., *Blood* 80:2548-2555, 1992). PCR amplification of cDNA from normal skin fails to show a signal for Tie receptor (Kaipainen et al., *Cancer Res.* 54:6571-6577, 1994). In contrast, a strong signal is seen with cDNA from metastasizing melanomas, where in situ studies localize this signal to the vascular endothelium. While Tie receptor expression is down-regulated in the established vasculature, it is upregulated in the angiogenesis that occurs in the ovary during ovulation, in wounds and in tumor (breast, melanoma and renal cell carcinoma) vasculature, consistent with prevailing views that angiogenesis in the adult borrows from embryonic angiogenic mechanisms.

b. Tie Knockout Animals

Homozygous mice with a Tie2 knockout, or carrying a transgene encoding a "dominant-negative" Tie2 receptor, confirmed that the Tie2 receptor is critical for embryonic development (Dumont et al., *Genes Dev.* 8:1897-1909, 1994; Sato et al., *Nature* 376:70-74, 1995). Embryonic death in these mice occurred due to vascular insufficiency and there were dramatically reduced numbers of endothelial cells. Vasculogenesis—that is the differentiation of endothelial cells and the in situ formation of vessels—appeared relatively normal in mice lacking Tie2. The subsequent sprouting and remodeling resulting in formation of vessel branches (angiogenesis) was drastically reduced in the Tie2 mutant mice embryos. This lack of sprouting and angiogenesis resulted in substantial growth retardation, particularly of the brain, neural tube and heart, resulting in lack of viability. This exemplifies the critical importance of Tie2 in angiogenesis. This is significant, as angiogenesis is regulated by a number of growth factors. Interestingly, Flk1 (VEGF receptor) knockout mice exhibit embryo lethal defects in vasculogenesis that occur earlier than those of Tie2 disruption. Disruption of the Tie1 receptor yields a much different, and later, defective phenotype; the mouse embryo dies late in development due to hemorrhage resulting from defective integrity of an otherwise well formed vasculature. Taken together, these studies suggest that the VEGF/Flk1 and Tie systems operate in sequential fashion, with Tie2 having a critical role in angiogenesis.

c. Tie2 Ligands

Recently, two ligands for the Tie2 receptor have been reported. Angiopoietin-1 binds and induces the tyrosine phosphorylation of Tie2 and its expression in vivo is in close proximity with developing blood vessels (Davis et al., *Cell* 87:1161-1169, 1996). Mice engineered to lack Angiopoietin-1 display angiogenic deficits reminiscent of those previously seen in mice lacking Tie2 receptors, demonstrating that Angiopoietin-1 is a primary physiologic ligand for Tie2 and that Tie2 has critical in vivo angiogenic actions (Suri et al., *Cell* 87:1171-1180, 1996). Angiopoietin-2 was identified by homology screening and shown to be a naturally occurring antagonist for Tie2 receptors. Transgenic overexpression of Angiopoietin-2 disrupts blood vessel formation in the mouse embryo (Maisonpierre et al., *Science* 277:55-60, 1997). Together, these results support a role for Tie2 receptors in angiogenesis.

In order to use the compounds of formula (I) in therapy, they will normally be formulated into a pharmaceutical composition in accordance with standard pharmaceutical practice.

According to a further aspect of the invention there is provided a pharmaceutical composition comprising a compound of formula (I) or a pharmaceutically acceptable salt thereof and a pharmaceutically acceptable carrier.

No toxicological effects are indicated/expected when a compound of formula (I) is administered in the above mentioned dosage range.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers is lactose, terra alba, sucrose, talc, gelatin, agar, pectin, acacia, magnesium stearate, stearic acid and the like. Exemplary of liquid carriers is syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably include a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

The compounds of Formula (I) may also be used topically in the treatment or prophylaxis of disease states exacerbated by excessive or inappropriate angiogenesis.

The compounds of Formula (I) are administered in an amount sufficient to inhibit Tie2 receptor activity such that it is regulated down to normal levels, or in some case to subnormal levels, so as to ameliorate or prevent the disease state.

Chronic diseases which have an inappropriate angiogenic component are various ocular neovasularizations, such as diabetic retinopathy and macular degeneration. Other chronic diseases which have an excessive or increased proliferation of vasculature are tumor growth and metastasis, atherosclerosis, and certain arthritic conditions. Therefore Tie2 tyrosine kinase receptor inhibitors will be of utility in the blocking of the angiogenic component of these disease states.

The term "excessive or increased proliferation of vasculature inappropriate angiogenesis" as used herein includes, but not limited to, diseases which are characterized by hemangiomas and ocular diseases. The term "inappropriate angiogenesis" as used herein includes, but not limited to, diseases which are characterized by vessel proliferation with accompanying tissue proliferation, such as occurs in cancer, metastasis, arthritis, psoriasis and atherosclerosis.

For all methods of use disclosed herein for the compounds of Formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen will be from about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a as defined number of days, can be ascertained by those skilled in the art using conventional course of treatment determination tests.

Pharmacological Test Methods

A. Measurement of Tie2 Kinase Activity

A partial cDNA clone for the Tie2 receptor was used to make protein for Tie kinase studies. In order to generate the primary screening assay, a baculovirus expressed GST fusion for Tie2 kinase domain was constructed and expressed using the commercial vector pAcG1 (Pharmingen).

This final construct was transfected into Baculovirus and soluble GST fusion products used in the screening assay. Prior work had demonstrated the use of a baculovirus expressed GST fusion for the murine Tie2 kinase domain to screen for candidate target/signaling molecules (Huang et al., Oncogene 11:2097-2103, 1995). Tie2 kinase activity assay: The Tie2 kinase activity assay was typically run in one of 2 ways described as follows. Minor variations in the assay give similar results.

1. Autophosphorylation flashplate assay

Materials:
Kinase buffer (final 20 mM Tris-HCl, pH7.0, 100 mM NaCl, 12 mM $MgCl_2$, 1 mM DTT).
Gamma $^{33}$p-ATP (usually final amount of 0.5-1 uCi/well)
ATP (final 30 uM, or other desired concentration)
Flashplate (96-well, polystyrene microplate with plastic scintillator coated wells)
TopCount (microplate scintillation counter)

Procedures:
Turn on incubator shaker and adjust temperature to 30° C.
Add 20 ul of 3× kinase buffer per well to the Flashplate
Add 20 ul of protein per well except for background. Compounds added, typically in DMSO stocks, at 1-2 ul.
Add 20 ul mixture of gamma $^{33}$p-ATP and cold ATP per well.

Total volume is 60 ul.
Cover with transparent polyester film.
Incubate at 30° C. for two hours in shaker, or desired time.
Take Flashplate out of the shaker, wash five times (for example, with 300 ul of 10 uM ATP in 1×PBS per well).
Read plate on TopCount or other counting instrument. Results are calculated as % inhibition
and IC50, using normal calculation methods.

2. Fluorescence Polarization for Tie 2 Kinase

Final Assay conditions:
  50 mM HEPES pH 7.5
  2% DMSO (when screening compounds)
  250 uM ATP
  2 mM $MgCl_2$
  1 mM DTT
  50 uM NaVanidate
  10 uM peptide substrate
  activated tie 2 kinase * see activation protocol below Peptide Substrate:
  RFWKYEFWR-OH
  MW (TFA salt)=1873 Da
  Make a 1 mM peptide stock and store at −20° C.
  Dilute to 100 uM just prior to use.

9× Kinase buffer:
  450 mM HEPES pH 7.5
  900 mM NaCl
  450 uM NaVanidate
  18 mM $MgCl_2$
  100 mM DTT
  Can be made up ahead of time and stored in aliquots at −20° C.

ATP stock:
  Make a 25 mM ATP stock and store in aliquots at −20° C. until needed. Dilute to 2.5 mM prior to use.

Procedure:
  For a 50 ul reaction add the following to each well of a 96-well black half-area plate (Costar, cat# 3694)
1. 5 ul of compound in 20% DMSO
2. 5 ul 9× kinase buffer.
3. 5 ul 2.5 mM ATP.
4. 5 ul 100 uM peptide substrate.
5. 25 ul PTK detection mix (Panvera, P-2652, 50 ml—UK distributor is Cambridge Bioscience)
6. 5 ul activated tie 2 kinase (protocol below) diluted in 1× buffer to initiate the reaction.
7. Read polarization on an FP instrument cycling for 30-50 minutes in accordance with enzyme activity.

Representative compounds of Formula (I), Examples 1 to 20 were found to be active in this fluorescence assay, having an IC50 of <1 uM.

Activation of Tie 2 Kinase Protocol:
Final Buffer Conditions:
  20 mM Tris-HCl pH 7.5
  12 mM $MgCl_2$
  100 mM NaCl
  20 uM NaVanidate
  1 mM DTT
  300 uM ATP Procedure
1. Incubate 5 uM tie 2 kinase in the 300 uM ATP and the buffering conditions described above.
2. Allow to incubate at 27° C. for 2 hours.
3. Add 2.5 ml reaction to a NAP-25 desalting column (Pharmacia Biotech cat. no. 17-0852-02) pre-equilibrated in 20 mM Tris-HCl pH 7.5, 100 mM $NaCl_2$ to separate the ATP from the enzyme.
4. Elute the enzyme with 5.0 ml 20 mM Tris-HCl pH 7.5, 100 mM $NaCl_2$; the protein concentration should be 2.5 uM at this point.
5. Aliquot out the enzyme and store at −80° C. as soon as possible.

B. Measurement of Tie2 Receptor Signal Transduction—a Cellular Assay

HEL cells (ATCC # TIB180) are cultured at between 1 and $5 \times 10^5$ ml in RPMI-1640 medium supplemented with 2 mM glutamine and 10% FBS as a suspension culture. Sixteen to thirty-six hours prior to an experiment, the necessary number of cells are passaged into 0.5% FBS/RPMI medium. On the day of an experiment, cells are harvested and resuspended at a density of $0.5-1.0 \times 10^7$ cells ml in 0.5% FBS RPMI and seeded at 2-3 ml/well in six well plates.

Alternatively, Human Umbilical Vein Endothelial Cells (HUVECs) (Clonetics—Walkersville, Md.) may be used for the assay. HUVECs between passages 2 and 12, are plated at $2 \times 10^5$ and $1 \times 10^6$ cells per well in a six well plate in supplemented EGM (Clonetics). After 24 hours the media is changed to EBM containing 3% BSA (Clonetics), and the cells are cultured overnight and used for assay the following day.

Cells are treated with inhibitory compounds at appropriate concentrations for 30-45 minutes. The contents of the wells are mixed briefly on a rocker (approx. 30 seconds) and then incubated at 37° C. The cells are then treated with a source of native ligand, such as serum or fibroblast conditioned medium for 10 minutes.

At the end of 10 minute incubation period the plate is placed on ice. The cells are harvested and the media is removed. The cells are lysed in denaturing sample buffer (Invitrogen—Carlsbad, Calif.). The suspension is sonicated for 5 pulses at a medium setting and returned to ice. The phosphorylation state of the Tie2 receptor is determined Western blotting and detection by an anti-phospho-Tie2 antibody, as detailed below (Harlow, E., and Lane, D. P., *Antibodies—A Laboratory Manual*, Cold Spring Harbor Laboratory Press: New York, 1988.). Thirty ul of the lysate are run on a 7.5% SDS/polyacrylamide gel. The gel is then transferred to a nitrocellulose or PVDF membrane as per the manufacturer's instructions for Western blotting.

The blots are washed with PBS 0.05% between-20 and then blocked with 3% BSA/PBS/Tween for 1 hour at room temperature. The blots are then incubated with 1 ug/ml anti-phospho-Tie2 antibody (SmithKline Beecham) in PBS/0.05% Tween for 1 hour. The blot is then washed 4 times with PBS/Tween for 5 minutes each. The blot is incubated with an anti-mouse-HRP conjugate secondary antibody at the dilution recommended by the manufacturer, in PBS/Tween for 1 hour. The blot is washed in PBS/Tween, 4 times for 5 minutes each. After the last wash, the blot is developed by the ECL method (Amersham) or some equivalent.

Using a densitometer or graphics program (e.g. ImageQuant—Molecular Dynamics), each blot is scanned. The Tie-2 band is isolated and "boxed out" for each lane. The pixel volume or comparable measure for each sample is analyzed. Also, an appropriate background region of the same dimensions is determined for each sample. After adjusting for background, phosphorylation is expressed as the ratio of phosphotyrosine staining, relative to the untreated control.

Angiogenesis In Vivo Model

Measurement of Angiogenesis In Vivo—Murine Air Pouch Granuloma Model:

Described below a model of inflammatory angiogenesis used to show that inhibition of Tie2 will stop the tissue destruction of excessive or inappropriate proliferation of blood vessels. The murine airpouch granuloma model of chronic inflammation (Kimura et al., 1985, J. Pharmacobio-Dyn., 8:393-400; Colville-Nash et al., 1995, *J. Pharm. and Exp. Ther.*, 274:1463-1472) whose disclosure is incorporated herein by reference in its entirety, is characterized by inflammatory cell influx, fibrous tissue proliferation and intense angiogenesis. It is representative of inflammatory angiogenesis and demonstrates that the angiogenic component can be pharmacologically modulated independently of granuloma growth and size. In addition, angiogenesis can be accurately quantitated by a vascular casting method.

Day 1, mice are anesthetized using Aerrane (isoflurane) gas (5%) or other approved methods, after which 3 mls of air is injected into the dorsal subcutaneous tissue using a 27 g needle. Mice are allowed to recover.

Day 0, mice are again anesthetized using Aerrane or other approved methods, once anesthetized 0.5 ml of Freunds complete adjuvant with 0.1% v/v croton oil is injected into the air pouch formed on Day-1. The animals also begin their dosing regime (number of day's dependent upon study) with the animals typically receiving compound in 0.2 ml N,N, Dimethyl Acetoacetamide(DMA) (Sigma, St. Louis, Mo.)/Cremephor El (Sigma, St. Louis, Mo.), saline (Oct. 10, 1980) or other appropriate vehicle. The animals are allowed to recover and all subsequent dosing is performed on the animals in the absence of anesthetics.

Days 1-5, animals are dosed according to schedule.

On Day 6 the animals are again anesthetized after which a vascular cast is made (Kimura et al., 1986, *J. Pharmacobio-Dyn.*, 9:442-446); this involves a 1 ml tail vein i.v. injection of a Carmine Red (10%) (Sigma, St. Louis, Mo.)/gelatin (5%) (Sigma, St. Louis, Mo.) solution. The animals are then sacrificed by lethal dose of anesthesia and chilled at 4° C. for 2 hours prior to the removal of the granuloma tissue.

When the granuloma is removed it is weighed and then dried for 3 days at 45° C. and reweighed. The dried tissue is then digested in 0.9 ml of a 0.05M phosphate buffer pH 7.0 containing 12 U/ml$^{-1}$ papain (Sigma, St. Louis, Mo.) and 0.33 g/L$^{-1}$ N-acetyl-1-Cysteine (Sigma, St. Louis, Mo.) at 57° C. for 3 days. After 3 days digestion the carmine red is solubilized by the addition of 0.1 ml 5 mM NaOH. Samples are centrifuged and then filtered using 0.2 um acrodiscs. The carmine content is then determined against a carmine red standard curve (0.5 to 2 mg/ml) generated in extracted tissue from non carmine treated animals and read at 490 nm. Sample and standard values are determined typically using DeltaSoft Elisa analysis software (Biometallics Inc., Princeton, N.J.). The carmine content is then used to determine the vascular indexes for the various treatments, vascular index being the mg carmine dye/gm dry tissue.

The effect of compounds on vascular density was typically measured for 6 days after induction of the granuloma. This time point has been determined to be at or near the peak of angiogenesis. As a positive control medroxyprogesterone, an angiostatic steroid (Gross et al., 1981, Proc. Natl. Acad. Sci. USA, 78:1176-1180), whose disclosure is hereby incorporated by reference in its entirety, was utilized. This control demonstrated a maximum reduction of 50% in this model. Medroxyprogesterone had no effect on granuloma size as measured by dry weight.

Angiogenesis Model—In Vivo

Measurement of Angiogenesis In Vivo—Matrigel Model:

Angiogenesis is modeled in-vivo by placing an extra-cellular matrix gel, beneath the skin of a mouse for approximately one week, and then employing several measures to quantitate angiogenic invasion of the gel (Biancone,L, et. al. Development of Inflammatory Angiogenesis by Local Stimulation of Fas In Vivo. J. Exp. Med. 186:147, 1997.). Briefly, reduced growth factor, endotoxin free Matrigel® (Becton-Dickinson, Bedford, Mass.) is a gel at low temperatures. Antibodies or known angiogenic agents are mixed with the gel, such that they do not constitute more than 2% of the total volume. Eight week old or older, C57 female mice are administered 0.5 ml of the Matrigel® by dorsal subcutaneous injection through chilled syringes. At physiological temperature, the liquid Matrigel® rapidly forms a solid and cohesive gel. During the course of the experiment, mice receive test compounds or controls administered as described above. After six days, the mice are sacrificed and the Matrigel® plugs recovered. Angiogenesis is quantitated by analyzing the hemoglobin content of the gel by the method of Drabkin (Drabkin, D L and Austin, J H: Spectrophotometric Studies II. Preparations from washed blood cells; nitric oxide hemoglobin and sulfhemoglobin. J Biol Chem 112:51, 1935.)(Sigma, St. Louis, Mo.), or by staining and quantitating blood vessel with CD31 staining as described above.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A compound selected from:
   2-tert-Butyl-4-naphthalen-2-yl-5-pyridin-4-yl-imidazole;
   2-tert-Butyl-4-(6-Ethoxynaphthalen-2-yl)-5-pyridin-4-yl-imidazole;
   4-(2-tert-Butyl-5-(6-methoxy-naphthalen-2-yl)-3H-imidazol-4-yl)-pyridine;
   2-tert-Butyl-4-Inden-2-yl-5-pyridin-4-yl-1H-imidazole;
   4-[2-tert-Butyl-5-(6-methoxy-naphthalen-2-yl)-1-methyl-1H-imidazol-4-yl]-pyridine;
or a pharmaceutically acceptable salts thereof.

2. A compound selected from:
   {4-[2-tert-Butyl-5-(6-methoxy-napthalen-2-yl)-3-H-imidazol-4-yl]-pyridin-2-yl}-N,N-diethyl-butane-1,4-diamine;
   {4-[2-tert-Butyl-5-(6-methoxy-napthalen-2-yl)-3-H-imidazol-4-yl]-pyridin-2-yl}-N,N-diethyl-ethane-1,2-diamine;
or a and pharmaceutically acceptable salts thereof.

3. A pharmaceutical composition comprising a compound according to claim 1, or a pharmaceutically acceptable salt thereof, and a pharmaceutically acceptable carrier.

4. A pharmaceutical composition comprising a compound according to claim 2, or a pharmaceutically acceptable salt thereof, and a pharmaceutically acceptable carrier.

5. A method of treating diabetic retinopathy comprising administering to a mammal an effective amount of a compound according to claim 1.

6. A method of treating diabetic retinopathy comprising administering to a mammal an effective amount of a compound according to claim 2.

* * * * *